US011896307B2

United States Patent
Tatara et al.

(10) Patent No.: US 11,896,307 B2
(45) Date of Patent: Feb. 13, 2024

(54) OPHTHALMOLOGIC APPARATUS AND METHOD OF CONTROLLING SAME

(71) Applicant: TOPCON CORPORATION, Tokyo (JP)

(72) Inventors: Yoko Tatara, Kita-ku (JP); Michiko Nakanishi, Katsushika-ku (JP); Shunichi Morishima, Kawagoe (JP)

(73) Assignee: TOPCON CORPORATION, Tokyo (JP)

( * ) Notice: Subject to any disclaimer, the term of this patent is extended or adjusted under 35 U.S.C. 154(b) by 873 days.

(21) Appl. No.: 16/937,607

(22) Filed: Jul. 24, 2020

(65) Prior Publication Data
US 2020/0352435 A1 Nov. 12, 2020

Related U.S. Application Data

(63) Continuation of application No. PCT/JP2019/000438, filed on Jan. 10, 2019.

(30) Foreign Application Priority Data

Mar. 27, 2018 (JP) ................................. 2018-059827

(51) Int. Cl.
*A61B 3/10* (2006.01)
*A61B 3/103* (2006.01)
*A61B 3/12* (2006.01)

(52) U.S. Cl.
CPC .............. *A61B 3/102* (2013.01); *A61B 3/103* (2013.01); *A61B 3/12* (2013.01)

(58) Field of Classification Search
CPC ............ A61B 3/102; A61B 3/103; A61B 3/12
(Continued)

(56) References Cited

U.S. PATENT DOCUMENTS

| 5,555,039 A | 9/1996 | Iki et al. |
| 2015/0320308 A1* | 11/2015 | Akiba ....................... A61B 3/14 382/131 |

(Continued)

FOREIGN PATENT DOCUMENTS

| EP | 3075303 A1 | 10/2016 | |
| EP | 3222204 A1 * | 9/2017 | ........... A61B 3/1005 |

(Continued)

OTHER PUBLICATIONS

Extended European search report dated Nov. 25, 2021, in corresponding European patent Application No. 19777093.6, 9 pages.

(Continued)

*Primary Examiner* — Joseph P Martinez
*Assistant Examiner* — Grant A Gagnon
(74) *Attorney, Agent, or Firm* — XSENSUS LLP

(57) ABSTRACT

An ophthalmologic apparatus includes a refractive power measurement optical system, a fixation projection system, an inspection optical system, and a controller. The refractive power measurement optical system includes a first focusing element capable of changing a focal position, and is configured to project first light onto a subject's eye and to detect returning light of the first light from the subject's eye via the first focusing element. The fixation projection system is configured to project fixation light target onto the subject's eye. The inspection optical system includes a second focusing element capable of changing a focal position in conjunction with the first focusing element, and is used for a predetermined inspection in which second light is projected onto at least the subject's eye via the second focusing element. The controller is configured to control the first focusing element and the second focusing element based on a detection result of the returning light, and to perform refractive power measurement using the first light in a state (Continued)

of promoting a fogging of the subject's eye by controlling the fixation projection system after performing the predetermined inspection by inspection optical system.

10 Claims, 6 Drawing Sheets

(58) Field of Classification Search
USPC .......................................................... 351/206
See application file for complete search history.

(56) References Cited

U.S. PATENT DOCUMENTS

| | | |
|---|---|---|
| 2019/0008378 A1 | 1/2019 | Hayashi et al. |
| 2020/0077888 A1 | 3/2020 | Hayashi et al. |

FOREIGN PATENT DOCUMENTS

| | | |
|---|---|---|
| EP | 3222204 A1 | 9/2017 |
| JP | 06-233741 A | 8/1994 |
| JP | 2016-150062 A | 8/2016 |
| JP | 2016-187461 A | 11/2016 |
| JP | 2017-042312 A | 3/2017 |
| JP | 2017-136215 A | 8/2017 |

OTHER PUBLICATIONS

Office Action dated Dec. 27, 2022 in corresponding Chinese Patent Application No. 201980012843.4 (with Computer-generated English Translation), 21 pages.
Japanese Office Action dated Apr. 19, 2022, in corresponding Japanese Patent Application No. 2018-059827, 6 pp.
International Search Report and Written Opinion dated Apr. 16, 2019 for PCT/JP2019/000438 filed on Jan. 10, 2019, 9 pages including English Translation of the International Search Report.
Japanese Office Action dated Sep. 27, 2022, in corresponding Japanese Patent Application No. 2018-059827, 6 pp.
Office Action dated Jun. 21, 2023, in corresponding Chinese patent Application No. 201980012843.4, 21 pages.

* cited by examiner

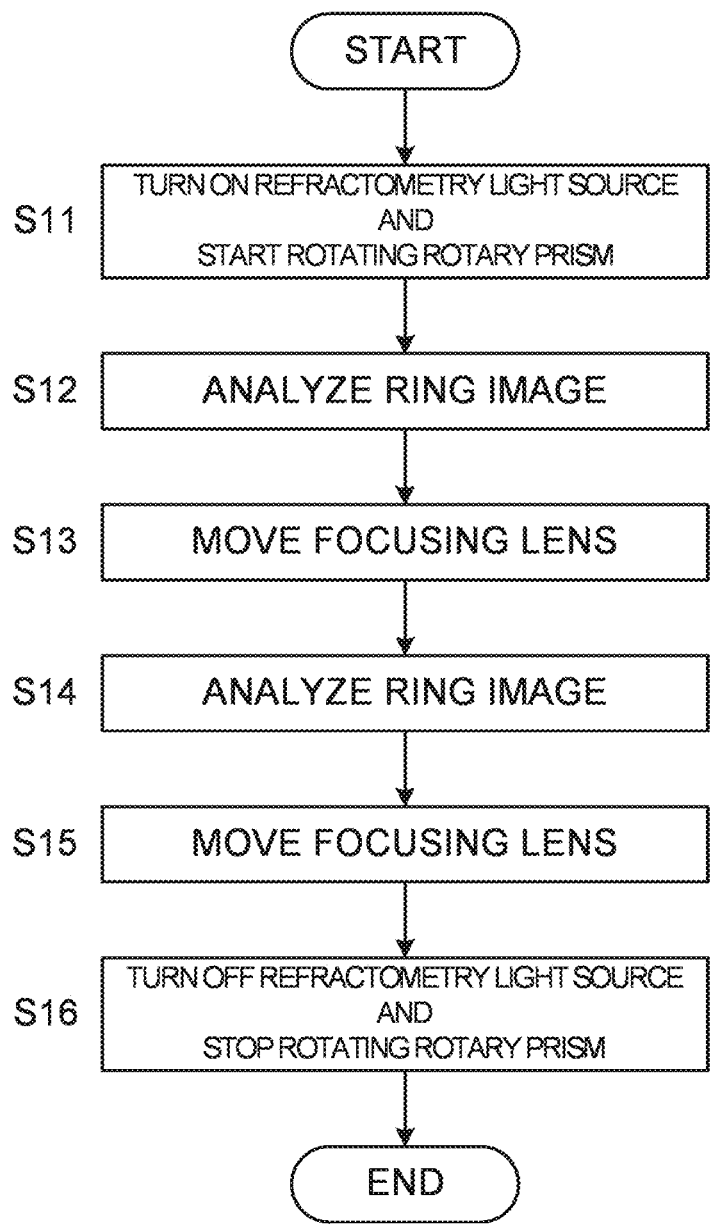

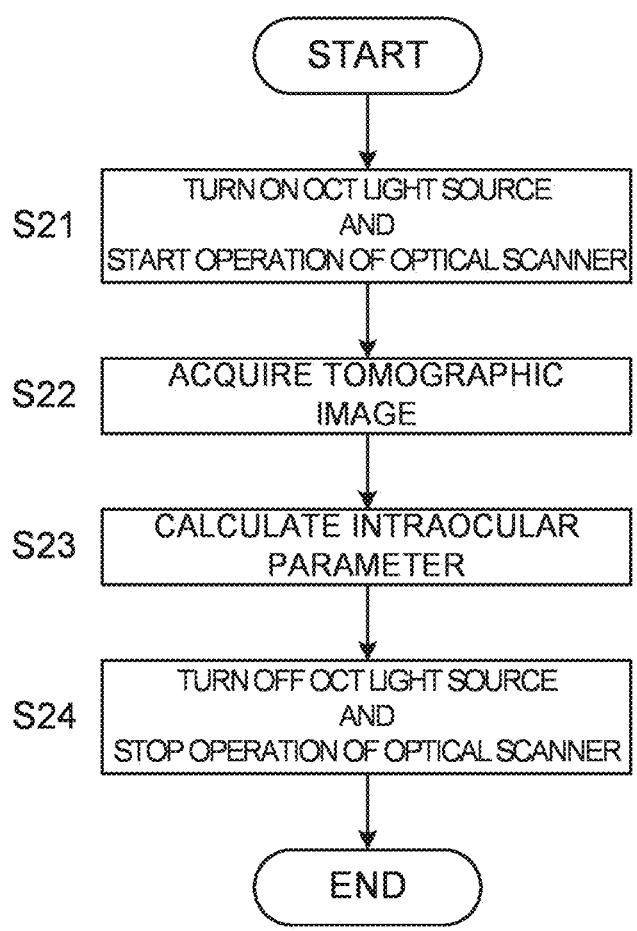

OPHTHALMOLOGIC APPARATUS AND METHOD OF CONTROLLING SAME

CROSS-REFERENCE TO RELATED APPLICATIONS

The present application is a continuation application of International Patent Application No. PCT/JP2019/000438, filed Jan. 10, 2019, which claims priority to Japanese Patent Application No. 2018-059827, filed Mar. 27, 2018. The contents of these applications are incorporated herein by reference in their entirety.

FIELD

The disclosure relates to an ophthalmologic apparatus and a method of controlling the same.

BACKGROUND

Ophthalmologic apparatuses capable of performing a plurality of inspections and measurements for a subject's eye are known. The inspections and the measurements for the subject's eye include a subjective inspection and an objective measurement. The subjective inspection is to acquire the result based on the responses from the subject. The objective measurement is to acquire information on the subject's eye mainly by the use of a physical method without referring to the responses from the subject.

For example, Japanese Unexamined Patent Publication No. 2017-136215 discloses an ophthalmologic apparatus capable of performing subjective inspection, refractive power measurement for the subject's eye and measurement using optical coherence tomography. In ophthalmologic apparatuses, a focusing position of light used for the inspection, the measurement, or the metering is specified every time the inspection or the like is performed, and the optical system is controlled so that the inspection or the like is performed at the specified focusing position. In such an ophthalmologic apparatus, focusing control is performed by cooperatively operating a plurality of focusing lenses provided in each optical system, and downsizing and simplification of control are achieved.

SUMMARY

Means of Solving the Problems

One aspect of some embodiments is an ophthalmologic apparatus, including: a refractive power measurement optical system including a first focusing element capable of changing a focal position, and configured to project first light onto a subject's eye and to detect returning light of the first light from the subject's eye via the first focusing element; a fixation projection system configured to project a fixation target onto the subject's eye; an inspection optical system including a second focusing element capable of changing a focal position in conjunction with the first focusing element, and configured to perform a predetermined inspection in which second light is projected onto at least the subject's eye via the second focusing element; and a controller configured to control the first focusing element and the second focusing element based on a detection result of the returning light, and to perform refractive power measurement using the first light in a state of promoting a fogging of the subject's eye by controlling the fixation projection system after performing the predetermined inspection using the inspection optical system.

Another aspect of some embodiments is a method of controlling an ophthalmologic apparatus including: a refractive power measurement optical system including a first focusing element capable of changing a focal position, and configured to project first light onto a subject's eye and to detect returning light of the first light from the subject's eye via the first focusing element; a fixation projection system configured to project a fixation target onto the subject's eye; and an inspection optical system including a second focusing element capable of changing a focal position in conjunction with the first focusing element, and configured to perform a predetermined inspection in which second light is projected onto at least the subject's eye via the second focusing element. The method of controlling the ophthalmologic apparatus includes: a focusing control step of controlling the first focusing element and the second focusing element based on a detection result of the returning light; an inspection step of controlling the inspection optical system to perform the predetermined inspection after the focusing control step; and a refractive power measurement step of performing refractive power measurement using the first light in a state of promoting a fogging of the subject's eye by controlling the fixation projection system, after the inspection step.

BRIEF EXPLANATION OF THE DRAWINGS

FIG. 5 is a schematic diagram illustrating a flow of the operation example of the ophthalmologic apparatus according to the embodiments.

FIG. 6 is a schematic diagram illustrating a flow of the operation example of the ophthalmologic apparatus according to the embodiments.

DETAILED DESCRIPTION

Figure 1:
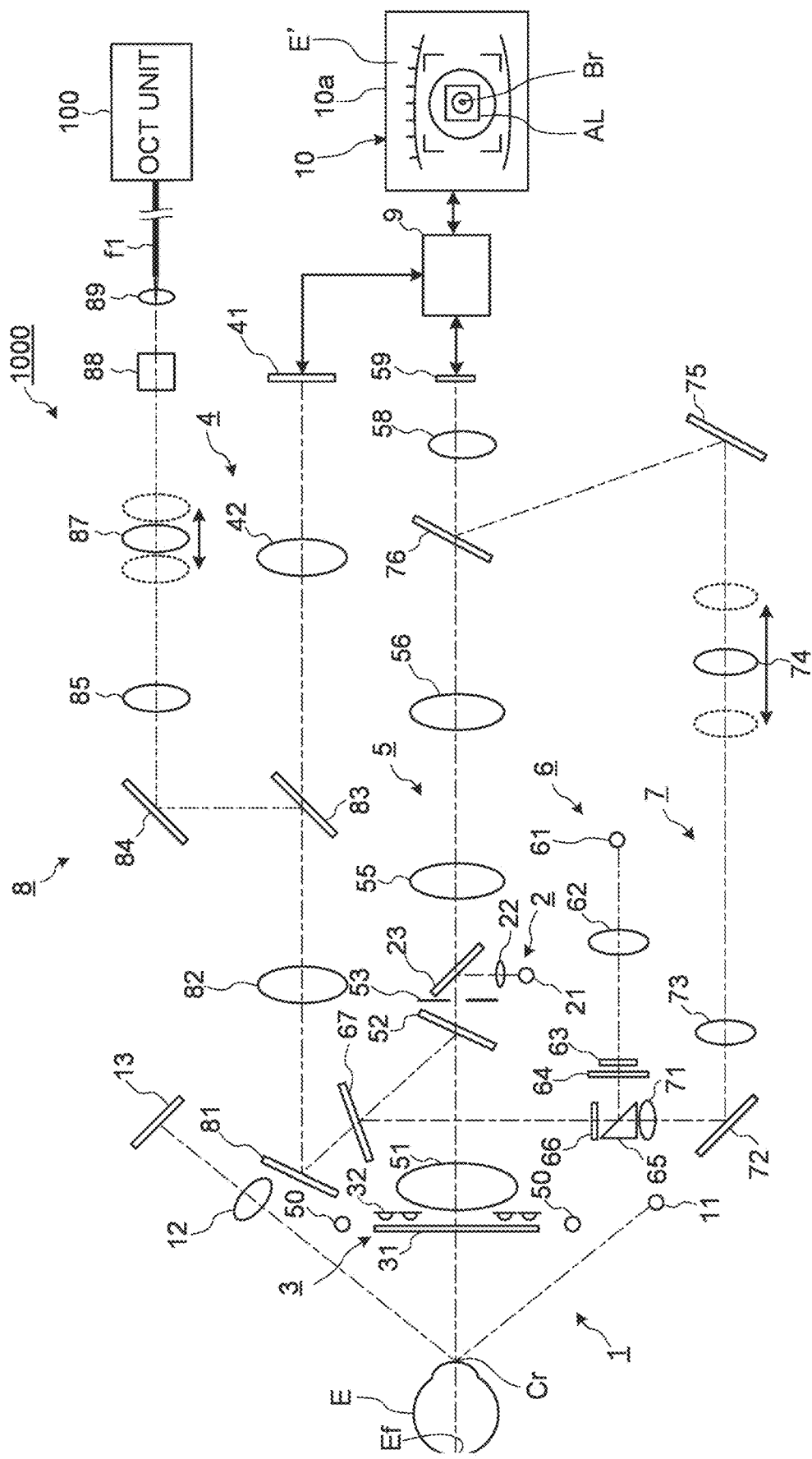
FIG. 1 is a schematic diagram illustrating an example of a configuration of an optical system of an ophthalmologic apparatus according to embodiments.

The refractive power measurement is performed in a state of promoting a fogging of the subject's eye. Therefore, in case of performing inspection or the like using another optical system after refractive power measurement (for example, measurement using optical coherence tomography), it is necessary to return the focusing state of another optical system to the state before the refractive power measurement. As a result, there is a problem that the time required for the inspection becomes long and the subject is burdened.

According to some embodiments according to the present invention, an ophthalmologic apparatus and a method of controlling the ophthalmologic apparatus capable of performing a plurality of inspections including refractive power measurement while reducing a burden on a subject with a simple configuration and control can be provided.

Referring now to the drawings, exemplary embodiments of an ophthalmologic apparatus and a method of controlling the ophthalmologic apparatus according to the present invention are described below. Any of the contents of the documents cited in the present specification and arbitrary known techniques may be applied to the embodiments below.

An ophthalmologic apparatus according to embodiments is capable of performing a plurality of inspections (measurements) including refractive power measurement for a subject's eye. Examples of an inspection other than the refraction power measurement includes an objective measurement other than the refraction power measurement and a subjective inspection (test).

The objective measurement is a method for measurement to acquire information on a subject's eye mainly by the use of a physical method without referring to the responses from the subject. The objective measurements include a measurement for acquiring the characteristics of the subject's eye and a photographing for acquiring an image of the subject's eye. Examples of the objective measurement include corneal shape measurement, tonometry, fundus imaging, and OCT measurement, in addition to the refractive power measurement.

The subjective inspection is a method for measurement to acquire information using the responses from the subject. Examples of the subjective inspection include a visual field test, and a subjective refractometry such as a far vision test, a near vision test, a contrast test, a glare test or the like.

The ophthalmologic apparatus according to the embodiments includes a refractive power measurement optical system for performing refractive power measurement, an inspection optical system for performing inspection other than the refractive power measurement, and a fixation projection system configured to project a fixation target onto the subject's eye. The refractive power measurement optical system includes a first focusing element capable of changing a focal position, and is configured to project first light onto a subject's eye and to detect returning light of the first light from the subject's eye via the first focusing element. The inspection optical system includes a second focusing element capable of changing a focal position in conjunction with the first focusing element, and is used for a predetermined inspection in which second light is projected onto at least the subject's eye via the second focusing element.

With such a configuration, the ophthalmologic apparatus can perform the inspection using the inspection optical system during the refractive power measurement. Specifically, the ophthalmologic apparatus controls the first focusing element and the second focusing element based on a refractive power of the subject's eye calculated based on the detection result of returning light of the first light, and performs refractive power measurement using the refractive power measurement optical system after performing a predetermined inspection using inspection optical system. The refractive power measurement is performed in a state of promoting a fogging of the subject's eye while projecting the fixation target onto the subject's eye using the fixation projection system.

In the following embodiments, the case where the inspection optical system is an OCT optical system for performing optical coherence tomography (hereinafter, referred to as OCT) on the subject's eye will be described. Further, hereinafter, a fundus conjugate position is a position substantially optically conjugate with a fundus of the subject's eye in a state where alignment is completed, and means a position optically conjugate with the fundus of the subject's eye or the vicinity of the position. Similarly, a pupil conjugate position is a position substantially optically conjugate with a pupil of the subject's eye in a state where alignment is completed, and means a position optically conjugate with the pupil of the subject's eye or the vicinity of the position.

<Configuration of Optical System>

FIG. 1 illustrates an example of the configuration of an optical system of the ophthalmologic apparatus according to the embodiments. The ophthalmologic apparatus 1000 according to the embodiments includes an optical system for observing the subject's eye E, an optical system for inspecting the subject's eye E, and a dichroic mirror that wavelength-separates the optical paths of these optical systems. An anterior segment observation system 5 is provided as the optical system for observing the subject's eye E. An OCT optical system, a refractometry optical system (refractive power measurement optical system), and the like are provided as the optical system for inspecting the subject's eye E.

The ophthalmologic apparatus 1000 includes a Z alignment system 1, a XY alignment system 2, a keratometry system 3, a fixation projection system 4, the anterior segment observation system 5, a refractometry projection system 6, a refractometry light reception system 7, and an OCT optical system 8. Hereinafter, for example, it is assumed that light with 940 nm to 1000 nm is used in the anterior segment observation system 5, light with 830 nm to 880 nm is used in the refractometry optical system (refractometry projection system 6, refractometry light reception system 7), light with 400 nm to 700 nm is used in the fixation projection system 4, and light with 1000 nm to 1100 nm is used in the OCT optical system 8.

(Anterior Segment Observation System 5)

The anterior segment observation system 5 is configured to acquire a moving image of an anterior segment of the subject's eye E. In an optical system passing through the anterior segment observation system 5, an imaging plane of an imaging element 59 is arranged at the pupil conjugate position. An anterior segment illumination light source 50 irradiates illumination light (for example, infrared light) on the anterior segment of the subject's eye E. Light reflected from the anterior segment of the subject's eye E passes through an objective lens 51, is transmitted through a dichroic mirror 52, passes through an aperture part formed in a diaphragm (telecentric diaphragm) 53, is transmitted through a half mirror 23, passes through relay lenses 55 and 56, and is transmitted through a dichroic mirror 76. The dichroic mirror 52 combines (or separates) the optical path of the refractometry optical system with the optical path of the anterior segment observation system 5. The dichroic mirror 52 is disposed so that its optical path combining surface for combining these optical paths is inclined with respect to the optical axis of the objective lens 51. The light penetrating the dichroic mirror 76 forms an image on an imaging surface of the imaging element 59 (area sensor) via an imaging lens 58. The imaging element 59 performs an imaging and a signal outputting at a predetermined rate. The output (video signal) of the imaging element 59 is input to a processor 9 described after. The processor 9 displays an anterior segment image E' based on this video signal on a display screen 10a of a display unit 10 described after. The anterior segment image E' is an infrared moving image for example.

(Z Alignment System 1)

The Z alignment system 1 is configured to project light (infrared light) for performing alignment in an optical axis direction (front-back directions, Z direction) of the anterior segment observation system 5 onto the subject's eye E. Light emitted from a Z alignment light source 11 is projected onto a cornea Cr of the subject's eye E, is reflected by the cornea Cr, and forms an image on a sensor surface of a line sensor 13 via an imaging lens 12. When the position of a corneal apex changes in the optical axis direction of the anterior segment observation system 5, the projected position of the light onto the sensor surface of the line sensor 13 changes. The processor 9 obtains a position of the corneal apex of the subject's eye E based on the projected position of the light onto the sensor surface of the line sensor 13 and controls a mechanism for moving the optical system to perform Z alignment based on this.

(XY Alignment System 2)

The XY alignment system 2 is configured to project light (infrared light) for performing alignment in a direction (left-right directions (X direction), up-down directions (Y direction)) orthogonal to the optical axis direction of the anterior segment observation system 5 onto the subject's eye E. The XY alignment system 2 includes a XY alignment light source 21 and a collimator lens 22 that are provided in an optical path branched from the optical path of the anterior segment observation system 5 by the half mirror 23. The light emitted from the XY alignment light source 21 passes through the collimator lens 22, is reflected by the half mirror 23, and is projected onto the subject's eye E through the anterior segment observation system 5. Reflected light from the cornea Cr of the subject's eye E is guided to the imaging element 59 through the anterior segment observation system 5.

An image (bright spot image) Br based on the reflected light is included in the anterior segment image E'. The processor 9 controls the display unit to display an alignment mark AL and the anterior segment image E' including the bright spot image Br on the display screen of the display unit. In the case of performing XY alignment manually, a user can perform an operation for moving the optical system so as to guide the bright spot image Br in the alignment mark AL. In the case of performing XY alignment automatically, the processor 9 controls a mechanism for moving the optical system so as to cancel a displacement of the bright spot image Br with respect to the alignment mark AL.

(Keratometry System 3)

The keratometry system 3 is configured to project a ring-shaped light flux (infrared light) for measuring a shape of the cornea Cr of the subject's eye E onto the cornea Cr. A keratometry plate (kerato plate) 31 is disposed between the objective lens 51 and the subject's eye E. A keratometry ring light source (kerato-ring light source, keratometry light source) 32 is provided on the back side (objective lens 51 side) of the keratometry plate 31. By illuminating the keratometry plate 31 with light from the keratometry ring light source 32, the ring-shaped light flux is projected onto the cornea Cr. The reflected light (keratometry ring image) from the cornea Cr of the subject's eye E is detected by the imaging element 59 along with the anterior segment image E'. The processor 9 calculates a corneal shape parameter representing a shape of the cornea Cr, by performing a known calculation based on this keratometry ring image.

(Refractometry Projection System 6 and Refractometry Light Reception System 7)

The refractometry optical system includes the refractometry projection system 6 and the refractometry light reception system 7 which are used for refractive power measurement. The refractometry projection system 6 is configured to project light flux (a ring-shaped light flux, for example) (infrared light) for measuring refractive power onto the fundus Ef. The refractometry light reception system 7 is configured to receive returning light of the light flux from the subject's eye E. The refractometry projection system 6 is provided in an optical path branched by a perforated prism 65 provided in an optical path of the refractometry light reception system 7. A hole part formed in the perforated prism 65 is arranged at the pupil conjugate position. In an optical system passing through the refractometry light reception system 7, the imaging surface of the imaging element 59 is arranged at the fundus conjugate position.

In some embodiments, the refractometry light source 61 is a SLD (Super Luminescent Diode) light source which is a high-intensity light source. The refractometry light source 61 is movable in an optical axis direction. The refractometry light source 61 is arranged at the fundus conjugate position. Light emitted from the refractometry light source 61 passes through the relay lens 62 and is incident on a conical surface of the conical prism 63. The light incident on the conical surface is deflected and emits from a bottom surface of the conical prism 63. The light emitted from the bottom surface of the conical prism 63 passes through a ring-shaped light transmission part formed in a ring diaphragm 64. The light (ring-shaped light flux) passing through the light transmission part of the ring diaphragm 64 is reflected on a reflective surface formed around the hole part of the perforated prism 65, passes through a rotary prism 66, and is reflected by the dichroic mirror 67. The light reflected by the dichroic mirror 67 is reflected by the dichroic mirror 52, passes through the objective lens 51, and is projected onto the fundus Ef. The rotary prism 66 is used for averaging the light quantity distribution of the ring-shaped light flux with respect to the blood vessel or the diseased site of the fundus Ef or for reducing the speckle noise caused by the light source.

Returning light of the ring-shaped light flux projected onto the fundus Ef passes through the objective lens 51, and is reflected by the dichroic mirrors 52 and 67. The returning light reflected by the dichroic mirror 67 passes through the rotary prism 66, passes through the hole part of the perforated prism 65, passes through a relay lens 71, is reflected by a reflective mirror 72, and passes through a relay lens 73 and a focusing lens 74. The focusing lens 74 is movable along an optical axis of the refractometry light reception system 7. The light passing through the focusing lens 74 is reflected by the reflective mirror 75, is reflected by a dichroic mirror 76, and forms an image on the imaging surface of the imaging element 59 via the imaging lens 58. The processor 9 calculates a refractive power value of the subject's eye E by performing the known calculation based on the output of the imaging element 59. In some embodiments, the refractive power value includes spherical power, astigmatic power, and astigmatic axis angle. In some embodiments, the refractive power value includes equivalent spherical power.

(Fixation Projection System 4)

The OCT optical system 8, which will be described later, is provided in the optical path wavelength-separated from the optical path of the refractometry optical system by the dichroic mirror 67. The fixation projection system 4 is provided in the optical path branched from the optical path of the OCT optical system 8 by the dichroic mirror 83.

The fixation projection system 4 is configured to present a fixation target to the subject's eye E. Under the control of the processor 9, the liquid crystal panel 41 displays a pattern representing the fixation target. By changing the display position of the fixation target on the screen of the liquid crystal panel 41, the fixation position of the subject's eye E can be changed. Examples of the fixation position of the subject's eye E include a position for acquiring an image centered at a macular region of the fundus Ef, a position for acquiring an image centered at an optic disc, and a position for acquiring an image centered at the fundus center between the macular region and the optic disc. The display position of the pattern representing the fixation target can be arbitrarily changed. Alternatively, instead of the liquid crystal panel 41, a transmissive visual target chart in which a visual target or the like is printed on a film or the like, a light source for illumination for illuminating the visual target chart may be provided.

Light from the liquid crystal panel 41 passes through a relay lens 42, penetrates a dichroic mirror 83, passes through a relay lens 82, is reflected by a reflective mirror 81, penetrates a dichroic mirror 67, and is reflected by the dichroic mirror 52. The light reflected by the dichroic mirror 52 passes through the objective lens 51 and is projected onto a fundus Ef. The liquid crystal panel 41 (or the liquid crystal panel 41 and the relay lens 42) is movable in the optical axis direction.

(OCT Optical System 8)

The OCT optical system 8 is an optical system for performing OCT measurement. The position of the focusing lens 87 is adjusted so that an end face of an optical fiber f1 and the fundus Ef are optically conjugate with each other based on the result of the refractometry performed before the OCT measurement.

The OCT optical system 8 is provided in the optical path wavelength-separated from the optical path of the refractometry optical system by the dichroic mirror 67. The optical path of the above fixation projection system 4 is coupled with the optical path of the OCT optical system 8 by the dichroic mirror 83. Thereby, the optical axes of the OCT optical system 8 and the fixation projection system 4 can be coupled coaxially.

Figure 2:
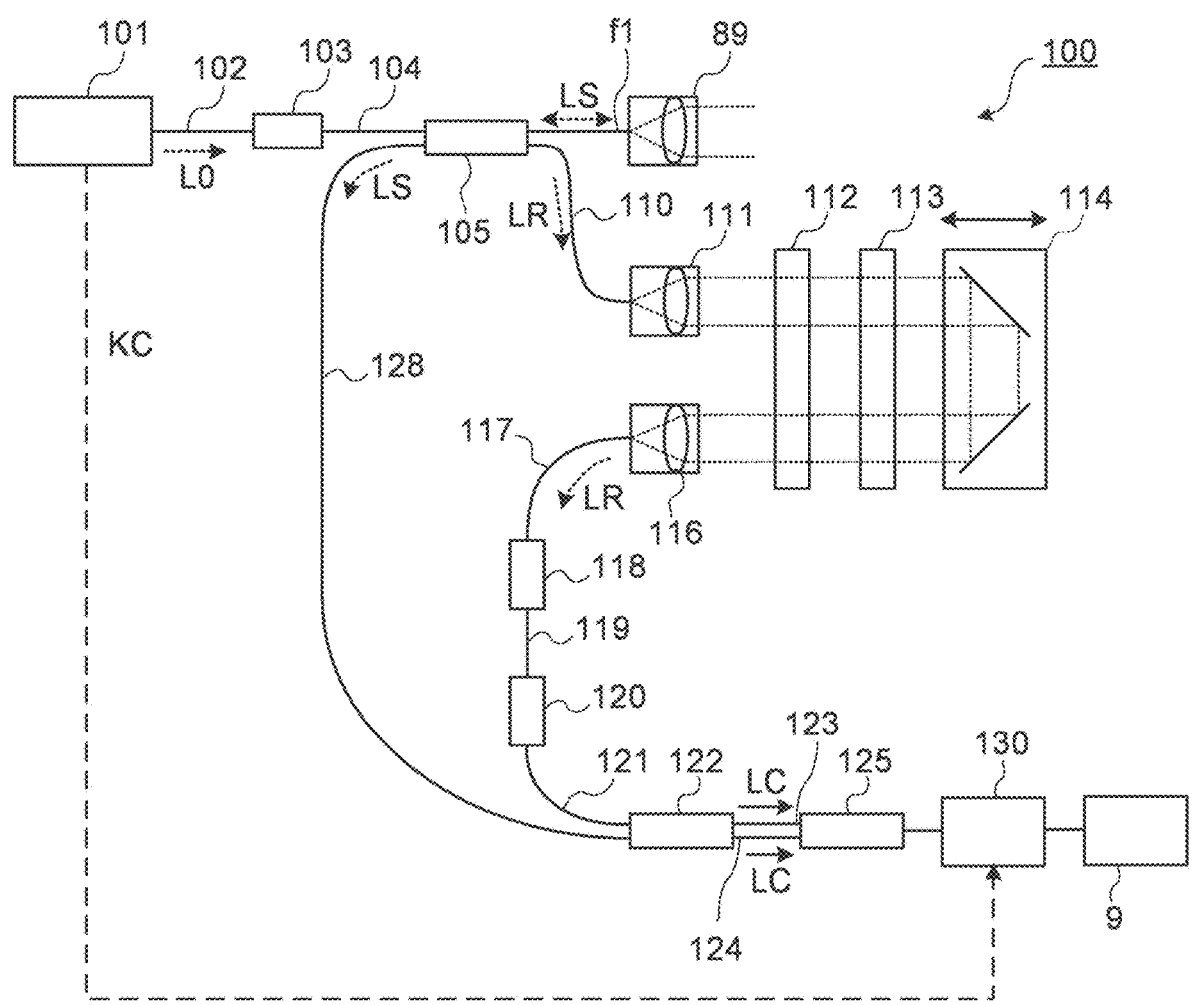
FIG. 2 is a schematic diagram illustrating an example of the configuration of the optical system of the ophthalmologic apparatus according to the embodiments.

The OCT optical system 8 includes an OCT unit 100. As illustrated in FIG. 2, in the OCT unit 100, like general swept-source-type OCT apparatuses, an OCT light source 101 includes a wavelength sweeping type (a wavelength scanning type) light source capable of sweeping (scanning) the wavelengths of emitted light. The wavelength sweeping type light source includes a laser light source that includes a resonator. The OCT light source 101 temporally changes the output wavelength in the near infrared wavelength band which cannot be visually recognized by the human eye.

As illustrated by an example in FIG. 2, the OCT unit 100 is provided with an optical system for performing swept source OCT. This optical system includes an interference optical system. This interference optical system has a function that splits light from the wavelength tunable type (wavelength sweeping type) light source into measurement light and reference light, a function that makes the returning light of the measurement light from the subject's eye E and the reference light having traveled through a reference optical path interfere with each other and generates interference light, and a function that detects the interference light. The detection result (detection signal) of the interference light obtained by the interference optical system is a signal indicating a spectrum of the interference light, and is sent to the processor 9.

The OCT light source 101 includes a near-infrared tunable laser which changes the wavelength of the emitted light (a wavelength range of 1000 nm to 1100 nm) at high speed, for example. The light L0 output from the OCT light source 101 is guided to the polarization controller 103 through the optical fiber 102, and the polarization state of the light L0 is adjusted. The light L0 whose polarization state has been adjusted is guided to the fiber coupler 105 through the optical fiber 104. The fiber coupler 105 splits the light L0 into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber f1, is made into the parallel light beam by the collimator lens unit 89, is reflected by the dichroic mirror 83 via an optical scanner 88, the focusing lens 87, a relay lens 85, and a reflective mirror 84.

The optical scanner 88 deflects the measurement light LS in a one-dimensionally or two-dimensional manner. The optical scanner 88 includes a first galvano mirror and a second galvano mirror, for example. The first galvano mirror deflects the measurement light LS so as to scan the fundus Ef in a horizontal direction orthogonal to the optical axis of the OCT optical system 8. The second galvano mirror deflects the measurement light LS deflected by the first galvano mirror so as to scan the fundus Ef in a vertical direction orthogonal to the optical axis of the OCT optical system 8. Examples of scan modes with the measurement light LS performed by the optical scanner 88 like this include horizontal scan, vertical scan, cross scan, radial scan, circle scan, concentric scan, helical (spiral) scan, and the like.

The measurement light LS reflected by the dichroic mirror 83 passes through the relay lens 82, is reflected by the reflective mirror 81, is transmitted through the dichroic mirror 67, is reflected by the dichroic mirror 52, is refracted by the objective lens 51, and is incident on the subject's eye E. The measurement light LS is scattered and reflected at various depth positions of the subject's eye E. The returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is a balanced photodiode, for example. The balanced photodiode includes a pair of photodetectors in which each photodiode detects each of the pair of interference light LC. The balanced photodiode outputs the difference between a pair of detection results acquired by the pair of photodetectors. The detector 125 sends the output (detection signal) to a DAQ (data acquisition system) 130.

The DAQ 130 is fed with a clock KC from the OCT light source 101. The clock KC is generated in the OCT light source 101 in synchronization with the output timing of each wavelength within a predetermined wavelength range performed by the wavelength tunable type light source. For example, the OCT light source 101 optically delays one of the two pieces of branched light obtained by branching the light L0 of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic processor 220 of the processor 9. For example, the arithmetic processor 220 performs the Fourier transform, etc. on the spectral distribution based on the sampling data for each series of wavelength scanning (i.e., for each A line). With this, the reflection intensity profile for each A line is formed. In addition, the arithmetic processor 220 forms image data by applying imaging processing to the reflection intensity profiles of the respective A lines.

In the present example, the corner cube 114 is provided for changing the length of the optical path of the reference light LR (reference optical path, reference arm); however, the difference between the measurement optical path length and the reference optical path length may be changed using another kind of optical member.

The processor 9 calculates the refractive power value from the result of the measurement obtained using the refractometry optical system, and controls the refractometry light source 61 and the focusing lens 74 to move respectively to positions where the fundus Ef, the refractometry light source 61, and the imaging element 59 are conjugate with each other, in the optical axis direction based on the calculated refractive power value. In some embodiments, the processor 9 controls the focusing lens 87 of the OCT optical system 8 to move in its optical axis direction in conjunction with the movement of the focusing lens 74. In some embodiments, the processor 9 controls the liquid crystal panel 41 to move in its optical axis direction in conjunction with the movement of the refractometry light source 61 and the focusing lens 74.

<Configuration of Processing System>

Figure 3:
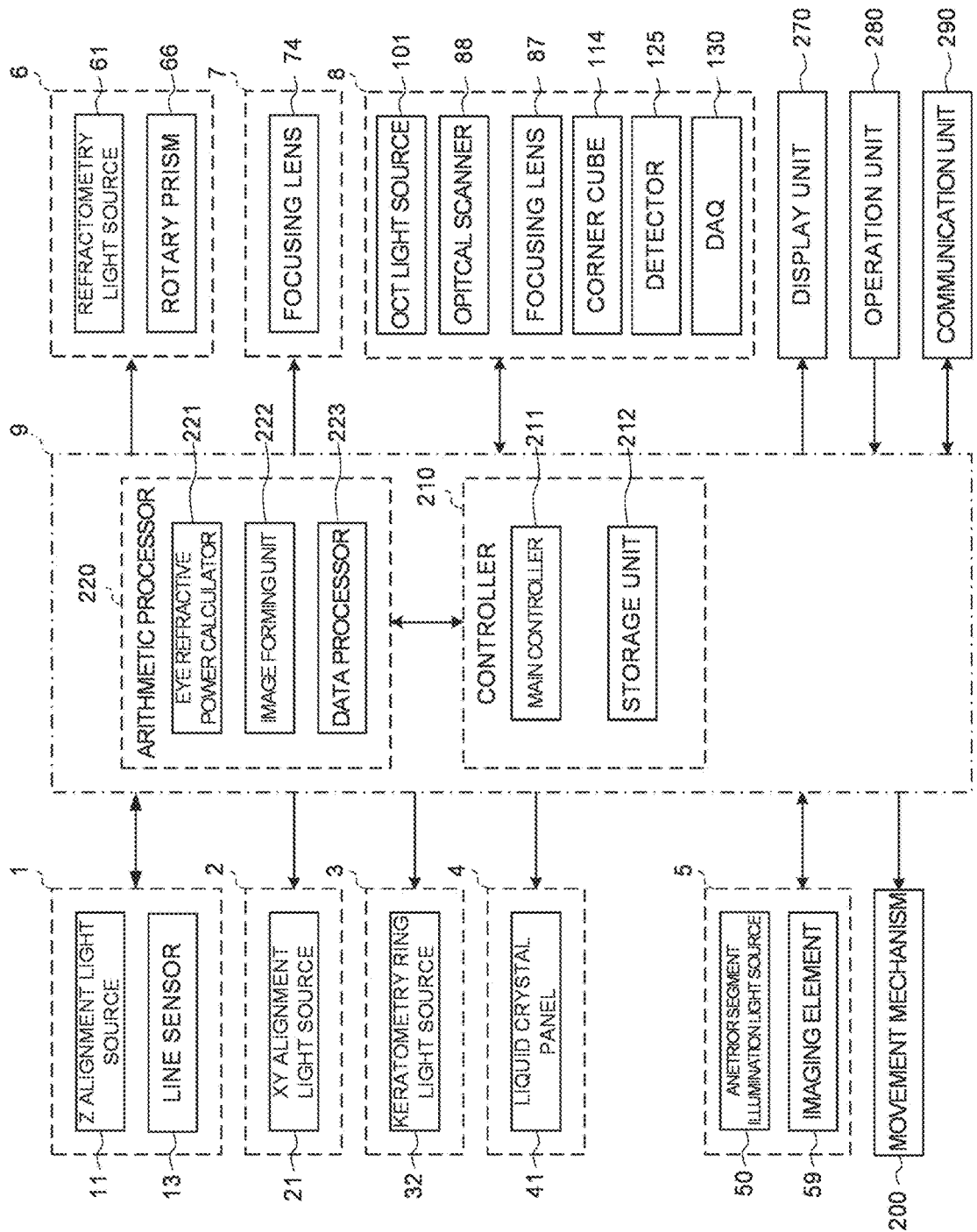
FIG. 3 is a schematic diagram illustrating an example of a configuration of a processing system of the ophthalmologic apparatus according to the embodiments.

The processing system of the ophthalmologic apparatus 1000 will be described. FIG. 3 illustrates an example of the functional structure of the processing system of the ophthalmologic apparatus 1000. FIG. 3 shows an example of a functional block diagram illustrating the processing system of the ophthalmologic apparatus 1000.

The processor (processing unit) 9 controls each part of the ophthalmologic apparatus 1000. Further, the processor 9 is capable of performing various types of arithmetic processing. The processor 9 includes a processor. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processor 9 realizes the function according to the embodiments, for example, by reading out a computer program stored in a storage circuit or a storage device and executing the computer program.

The processor 9 includes a controller 210 and the arithmetic processor 220. The processor 9 includes one or more processors that realize the functions of the controller 210 and the arithmetic processor 220. For example, the processor 9 includes a control processor that realizes the function of the controller 210 and an arithmetic processing processor that realizes the function of the arithmetic processor 220. Further, the ophthalmologic apparatus 1000 includes a movement mechanism 200, a display unit 270, an operation unit 280, and a communication unit 290.

The movement mechanism 200 is a mechanism for moving a head unit in front, back, left and right directions, the head unit housing the optical systems such as the Z alignment system 1, the XY alignment system 2, the keratometry system 3, the fixation projection system 4, the anterior segment observation system 5, the refractometry projection system 6, the refractometry light reception system 7, the OCT optical system 8, and the like. For example, the movement mechanism 200 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The controller 210 (main controller 211) controls the movement mechanism 200 by sending a control signal to the actuator.

(Controller 210)

The controller 210 includes a processor and controls each part of the ophthalmologic apparatus. The controller 210 includes the main controller 211 and a storage unit 212. The storage unit 212 stores, in advance, a computer program for controlling the ophthalmologic apparatus. The computer program includes programs for controlling light source, programs for controlling detector, programs for controlling optical scanner, programs for controlling optical system, programs for arithmetic processing, programs for user interface, and the like. The main controller 211 operates according to the computer programs, and thereby the controller 210 performs the control processing.

The main controller 211 performs various controls of the ophthalmologic apparatus, as a measurement controller. Examples of control for the Z alignment system 1 include control of the Z alignment light source 11, control of the line sensor 13, and the like. Examples of the control of the Z alignment light source 11 include turning on and off of the light source, adjustment of an amount of light, adjustment of aperture, and the like. Examples of the control of the line sensor 13 include adjustment of exposure of a detecting element, adjustment of gain of the detecting element, adjustment of detecting rate of the detecting element, and the like. Thereby, the Z alignment light source 11 can be switched between lighting and non-lighting or the amount of light can be changed. The main controller 211 acquires a signal detected by the line sensor 13 and specifies the projected position of light onto the line sensor 13 based on the acquired signal. The main controller 211 obtains a position of a corneal apex of the subject's eye E based on the specified projected position and controls the movement mechanism 200 based on the specified position to move the head unit in front and back directions (Z alignment).

Examples of control for the XY alignment system 2 include control of the XY alignment light source 21, and the like. Examples of the control of the XY alignment light source 21 include turning on and off of the light source, adjustment of an amount of light, adjustment of aperture, and the like. Thereby, the XY alignment light source 21 can be switched between lighting and non-lighting, or the amount of light can be changed. The main controller 211 acquires a signal detected by the imaging element 59, and specifies a position of a bright spot image on the basis of returning light of the light from the XY alignment light source 21 based on the acquired signal. The main controller 211 controls the movement mechanism 200 to move the head unit in left, right, up, down directions so as to cancel a displacement the position of the bright spot image with respect to a predetermined target position (for example, a center position of the alignment mark AL) (XY alignment).

Examples of control for the keratometry system 3 include control of the keratometry ring light source 32, and the like. Examples of the control of the keratometry ring light source 32 include turning on and off of the light source, adjustment of an amount of light, adjustment of aperture, and the like. Thereby, the keratometry ring light source 32 can be switched between lighting and non-lighting, or the amount of light can be changed. The main controller 211 controls the arithmetic processor 220 to perform a known calculation on a keratometry ring image detected by the imaging element 59. Thereby, corneal shape parameters of the subject's eye E are obtained.

Examples of control for the fixation projection system 4 include control of the liquid crystal panel 41 and the like. Examples of the control of the liquid crystal panel 41 include displaying on and off of the fixation target, switching the display position of the fixation target, and the like. Thereby, the fixation target is projected onto the fundus Ef of the subject's eye E. For example, the fixation projection system 4 includes a movement mechanism that moves the liquid crystal panel 41 (or the liquid crystal panel 41 and the relay lens 42) in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move at least the liquid crystal panel 41 in the optical axis direction. Thereby, the position of liquid crystal panel 41 is adjusted so that the liquid crystal panel 41 and the fundus Ef are optically conjugate with each other.

Examples of the control for the anterior segment observation system 5 include control of an anterior segment illumination light source 50, control of the imaging element 59, and the like. Examples of the control of the anterior segment illumination light source 50 include turning on and off the light sources, adjustment of light amount, adjustment of apertures, and the like. Thereby, the anterior segment illumination light source 50 can be switched between lighting and non-lighting, or light amount can be changed. Example of the control of the imaging element 59 include adjustment of exposure of the imaging element 59, adjustment of gain of the imaging element 59, adjustment of detecting rate of the imaging element 59, and the like. The main controller 211 acquires a signal detected by the imaging element 59 and controls the arithmetic processor 220 to perform processing such as forming image based on the acquired signal and the like.

Examples of control for the refractometry projection system 6 include control of the refractometry light source 61, control of the rotary prism 66, and the like. Examples of the control of the refractometry light source 61 include turning on and off of the light source, adjustment of an amount of light, adjustment of aperture, and the like. Thereby, the refractometry light source 61 can be switched between lighting and non-lighting, or the amount of light can be changed. For example, the refractometry projection system 6 includes a movement mechanism that moves the refractometry light source 61 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the refractometry light source 61 in the optical axis direction. Examples of the control of the rotary prism 66 include control of rotating the rotary prism 66 and the like. For example, a rotary mechanism that rotates the rotary prism 66 is provided and the main controller 211 controls the rotary mechanism to rotate the rotary prism 66.

Examples of control for refractometry light reception system 7 include control of the focusing lens 74, and the like. Examples of the control of the focusing lens 74 include control of moving the focusing lens 74 in the optical axis direction. For example, the refractometry light reception system 7 include a movement mechanism that moves the focusing lens 74 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 74 in the optical axis direction. The main controller 211 is capable of moving the refractometry light source 61 and the focusing lens 74 in the optical axis direction respectively depending on the refractive power of the subject's eye E for example so that the refractometry light source 61 and the fundus Ef and the imaging element 59 are optically conjugate with each other.

Examples of control for the OCT optical system 8 include control of the OCT light source 101, control of the optical scanner 88, control of the focusing lens 87, control of the corner cube 114, control of the detector 125, control of the DAQ 130, and the like. Examples of the control of the OCT light source 101 includes turning on and off of the light source, adjustment of an amount of light, adjustment of aperture, and the like. Examples of the control of the optical scanner 88 include control of the scanning position and the scan range and the scanning speed by means of the first galvano mirror, control of the scanning position and the scan range and the scanning speed by means of the second galvano mirror, and the like. Examples of the control of the focusing lens 87 include control of moving the focusing lens 87 in the optical axis direction. For example, the OCT optical system 8 include a movement mechanism that moves the focusing lens 87 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 87 in the optical axis direction. In some embodiments, the ophthalmologic apparatus is provided with a holding member that holds the focusing lens 74 and the focusing lens 87, and the driver that drives the holding member. The main controller 211 controls the driver to move the focusing lenses 74 and 87. For example, the main controller 211 may moves the focusing lens 87 alone based on the intensity of the interference signal, after moving the focusing lens 87 in conjunction with the movement of the focusing lens 74. Examples of the control of the corner cube 114 include control of moving the corner cube 114 along the optical path of the corner cube 114. For example, the OCT optical system 8 include a movement mechanism that moves the corner cube 114 along the optical path. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the corner cube 114 along the optical path. Examples of the control of the detector 125 include adjustment of exposure of a detecting element, adjustment of gain of a detecting element, adjustment of detecting rate of a detecting element, and the like. The main controller 211 controls the DAQ 130 to perform sampling of the signal detected by the detector 125 and controls the arithmetic processor 220 (image forming unit 222) to perform processing such as forming image based on the sampled signal and the like.

Further, the main controller 211 performs a process of writing data in the storage unit 212 and a process of retrieving data from the storage unit 212.

(Storage Unit 212)

The storage unit 212 stores various types of data. Examples of the data stored in the storage unit 212 include a measurement result of the objective measurement, image data of a tomographic image, image data of a fundus image, subject's eye information, and the like. The subject's eye information includes information on the subject such as patient ID and name, and information on the subject's eye such as identification information of the left eye/right eye. The storage unit 212 further stores various types of programs and data to run the ophthalmologic apparatus.

(Arithmetic Processor 220)

The arithmetic processor 220 includes an eye refractive power calculator 221, the image forming unit 222, and a data processor 223. The arithmetic processor 220 includes one or more processors that realize the functions of the eye refractive power calculator 221, the image forming unit 222, and the data processor 223. For example, the arithmetic processor 220 includes a processor that realizes the function of the eye refractive power calculator 221, an image forming processor that realizes the function of the image forming unit 222, and a data processing processor that realizes the function of the data processor 223.

The eye refractive power calculator 221 analyzes a ring image (pattern image) acquired by receiving the returning light of the ring-shaped light flux (ring-shaped measurement pattern) by the imaging element 59, the ring-shaped light flux being projected onto the fundus Ef by the refractometry projection system 6. For example, the eye refractive power calculator 221 obtains a position of the center of gravity of the ring image from the brightness distribution in the image representing the acquired ring image, obtains brightness distributions along a plurality of scanning directions extending radially from the position of the center of gravity, and specifies a ring image from these brightness distributions. Subsequently, the eye refractive power calculator 221 obtains an approximate ellipse of the specified ring image and obtains a spherical power, an astigmatic power, and an astigmatic axis angle by assigning a major axis and a minor axis of the approximate ellipse to a known formula. Alternatively, the eye refractive power calculator 221 can obtain the eye refractive power parameter based on deformation and displacement of the ring image with respect to the reference pattern.

Further, the eye refractive power calculator 221 calculates a corneal refractive power, a corneal astigmatism power, and a corneal astigmatic axis angle based on the keratometry ring image acquired by the anterior segment observation system 5. For example, the eye refractive power calculator 221 calculates a corneal curvature radius of the steepest meridian and/or the flattest meridian of the anterior surface of the cornea by analyzing the keratometry ring image and calculates above parameters based on the corneal curvature radius.

The image forming unit 222 forms image data of a tomographic image of the fundus Ef based on a signal detected by the detector 125. That is, the image forming unit 222 forms the image data of the subject's eye E based on a detection result of the interference light LC obtained by the interference optical system. Like the conventional spectral-domain-type OCT, this process includes processes such as filtering and FFT (Fast Fourier Transform). The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

The data processor 223 performs various kinds of data processing (e.g., image processing) and various kinds of analysis on a tomographic image formed by the image forming unit 222. For example, the data processor 223 performs various correction processes such as brightness correction and dispersion correction of images. Further, the data processor 223 performs various types of image processing and analysis on images (anterior segment image, etc.) acquired using the anterior segment observation system 5.

The data processor 223 can form volume data (voxel data) of the subject's eye E by performing known image processing such as interpolation processing for interpolating pixels between tomographic images. In the case of displaying an image based on the volume data, the data processor 223 performs rendering processing on the volume data so as to form a pseudo three-dimensional image viewed from a specific line-of-sight direction.

(Display Unit 270, Operation Unit 280)

Upon receiving control of the controller 210, the display unit 270 displays information, as a user interface unit. The display unit 270 includes the display unit 10 as illustrated in FIG. 1 and the like.

The operation unit 280 is used to operate the ophthalmologic apparatus, as the user interface unit. The operation unit 280 includes various types of hardware keys (the joystick, buttons, switches, etc.) provided in the ophthalmologic apparatus. Further, the operation unit 280 may include various kinds of software keys (buttons, icons, menus, etc.) displayed on the touch panel type display screen 10a.

At least part of the display unit 270 and the operation unit 280 may be integrally configured. A typical example of this is the touch-panel display screen 10a.

(Communication Unit 290)

The communication unit 290 has the function of communicating with an external device (not shown). The communication unit 290 includes a communication interface according to the mode of communication with an external device. Examples of the external device includes an eyeglass lens measurement device for measuring the optical properties of lenses. The eyeglass lens measurement device measures the lens power of eyeglasses worn by a subject and the like, and feeds the measurement data to the ophthalmologic apparatus 1000. The external device may also be a device (reader) having the function of reading information from a recording medium or a device (writer) having the function of writing information to a recording medium. Further, the external device may be a hospital information system (HIS) server, a Digital Imaging and Communications in Medicine (DICOM) server, a doctor terminal, a mobile terminal, a personal terminal, a cloud server, or the like. The communication unit 290 may be provided in the processor 9, for example.

The focusing lens 74 is an example of the "first focusing element capable of changing a focal position" according to the embodiments. The light output from the refractometry light source 61 is an example of the "first light" according to the embodiments. The refractometry optical system or the OCT optical system 8 is an example of the "refractive power measurement optical system" according to the embodiments. The focusing lens 87 is an example of the "second focusing element capable of changing a focal position in conjunction with the first focusing element" according to the embodiment. The measurement light LS is an example of the "second light" according to the embodiments. The OCT optical system 8 is an example of the "inspection optical system" according to the embodiments. The liquid crystal panel 41 is an example of "display unit" according to the embodiments.

Operation Example

The operation of the ophthalmologic apparatus 1000 according to the embodiments will be described.

Figure 4:
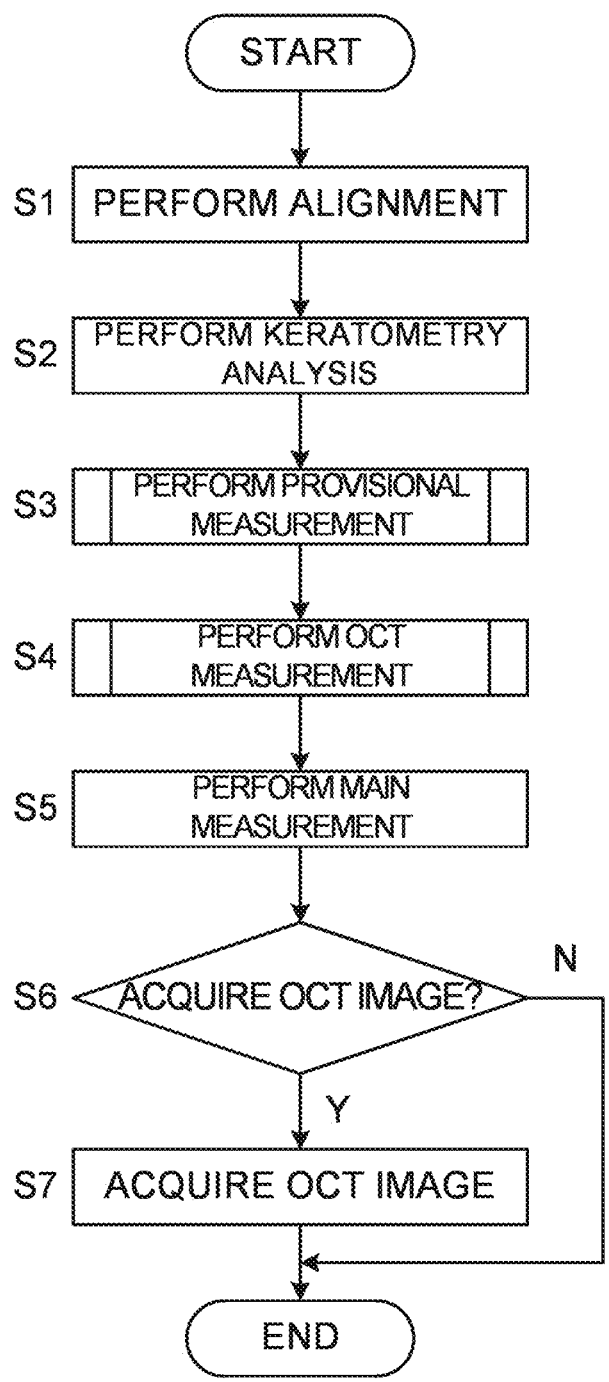
FIG. 4 is a schematic diagram illustrating a flow of the operation example of the ophthalmologic apparatus according to the embodiments.

FIGS. 4 to 6 illustrate examples of the operation of the ophthalmologic apparatus 1000. FIG. 4 shows a flowchart of an example of the operation of the ophthalmologic apparatus 1000. FIG. 5 shows a flowchart of an example of the operation of step S3 in FIG. 4. FIG. 6 shows a flow chart of an example of the operation of step S4 in FIG. 4. The storage unit 212 stores computer programs for realizing the processing shown in FIGS. 4 to 6. The main controller 211 operates according to the computer programs, and thereby the main controller 111 performs the processing shown in FIGS. 4 to 6.

(S1: Perform Alignment)

When the examiner performs a predetermined operation on the operation unit 280 in a state where the face of the subject is fixed to a face supporter (not shown), the ophthalmologic apparatus 1000 performs alignment.

Specifically, the main controller 211 turns on the Z alignment light source 11 and the XY alignment light source 21. Furthermore, the main controller 211 turns on the anterior segment illumination light source 50. The processor 9 acquires imaging signal of an anterior segment image formed on the imaging surface of the imaging element 59 and controls the display unit 270 to display the anterior segment image. After that, the optical system shown in FIG. 1 is moved to at the inspection position of the subject's eye E. The inspection position is a position where the inspection of the subject's eye E can be performed with sufficient accuracy. The subject's eye E is placed at the inspection position through the alignment described above (that is, by the use of the Z alignment system 1, the XY alignment system 2, and the anterior segment observation system 5). The movement of the optical system is performed by the controller 210 according to operation or instruction from a user, or instruction by the controller 210. That is, the movement of the optical system to the inspection position of the subject's eye E and the preparation for the objective measurement are carried out.

Further, the main controller 211 moves the refractometry light source 61, the focusing lens 74, and the liquid crystal panel 41 along the respective optical axes to the origin positions (for example, the position corresponding to OD).

(S2: Perform Keratometry Analysis)

Next, the main controller 211 controls the liquid crystal panel 41 to display the pattern representing the fixation target at a display position corresponding to the desired fixation position. Thereby, the subject's eye E is gazed at the desired fixation position.

After that, the main controller 211 turns on the keratometry ring light source 32. When the light is emitted from the keratometry ring light source 32, a ring-shaped light flux for corneal shape measurement is projected onto the cornea Cr of the subject's eye E. The eye refractive power calculator 221 applies arithmetic processing to the image acquired by the imaging element 59 to calculate the corneal curvature radius. Furthermore, based on the calculated corneal curvature radius, the eye refractive power calculator 221 calculates the corneal refractive power, the corneal astigmatic power, and the corneal astigmatic axis angle. The calculated corneal refractive power and the like are stored in the storage unit 212 in the controller 210. Upon reception of an instruction from the main controller 211, an operation or instruction on the operation unit 280 by the user, the operation of the ophthalmologic apparatus 1000 proceeds to step S3. It should be noted that this keratometry analysis may be performed simultaneously with the main measurement in step S5 or continuously with the main measurement in step S5.

(S3: Perform Provisional Measurement)

Next, the main controller 211 controls the liquid crystal panel 41 to project the fixation target onto the subject's eye E and starts the refractometry. In the present embodiments, the refractometry includes a provisional measurement and a main measurement. In the provisional measurement, a focusing state in the refractometry optical system is changed in accordance with a refractive power of the subject's eye E. In the main measurement, the refractive power of the subject's eye E is obtained while promoting the fogging with reference to the focusing state changed in the provisional measurement.

In step S3, each of the refractometry light source 61, the focusing lenses 74 and 87 is moved in the optical axis direction and is arranged at a position corresponding to the refractive power of the subject's eye E. Details of step S3 will be described later.

(S4: Perform OCT Measurement)

Subsequently, the main controller 211 moves the corner cube 114 to correct the optical path length so that a desired OCT image of the eye can be obtained in a state where the focusing lens 87 is moved in step S3, and performs OCT measurement by controlling the OCT optical system 8. That is, OCT measurement is performed while the refractometry. Thereby, OCT measurement is performed before promoting the fogging of the subject's eye E. Therefore, the focusing control for performing OCT measurement becomes unnecessary, and the measurement time can be shortened. It should be noted that the correction of the optical path length for moving the corner cube 114 may be performed in parallel in step 3 by automatically adjusting the position of the OCT image. Details of step S4 will be described later.

Upon reception of an instruction from the main controller 211, an operation or instruction on the operation unit 280 by the user, the operation of the ophthalmologic apparatus 1000 proceeds to step S5.

(S5: Perform Main Measurement)

In step S5, the main controller 211 promotes the fogging of the subject's eye E by further moving the liquid crystal panel 41 form the position obtained in the provisional measurement to the fogging position. After that, the main controller 211 turns on the refractometry light source 61 in case that the refractometry light source 61 has been off. In addition, the main controller 211 starts rotating the rotary prism 66 in case that the rotation of the rotary prism 66 is stopped. Subsequently, the main controller 211 controls the refractometry projection system 6 and the refractometry light reception system 7 to acquire a ring image again, similar to the provisional measurement. The main controller 211 controls the eye refractive power calculator 221 to calculate a spherical power, an astigmatic power, and an astigmatic axis angle from the analysis result obtained of the ring image and the movement amount of the focusing lens 74. The calculated spherical power, the astigmatic power, and the astigmatic axis angle are stored in the storage unit 212.

(S6: Acquire OCT Image?)

Next, the main controller 211 determines whether or not to acquires the OCT image. The main controller 211 determines whether or not to acquire the OCT image according to an instruction from the main controller 211, an operation or instruction to the operation unit 280 by the user. For example, in case that the time required for OCT measurement such as 3D scanning becomes long, the burden on the subject can be reduced by acquiring the OCT image after step S5.

When it is determined that the OCT image is to be acquired (S6: Y), the operation of the ophthalmologic apparatus 1000 proceeds to step S7. When it is determined that the OCT image is not to be acquired (S6: N), the ophthalmologic apparatus 1000 terminates the operation (END).

(S7: Acquire OCT Image)

When it is determined that the OCT image is to be acquired (S6: Y), the main controller 211 returns a position of the liquid crystal panel 41, which has been moved to the fogging position in step S5, to a focusing position obtained in the provisional measurement of step S3. After that, the main controller 211 controls the liquid crystal panel 41 to project the fixation target onto the subject's eye E and performs the OCT measurement.

The main controller 211 turns on the OCT light source 101 and controls the optical scanner 88 so as to scan a predetermined site of the fundus Ef with the measurement light LS. A detection signal obtained by scanning with the measurement light LS is fed to the image forming unit 222. The image forming unit 222 forms a tomographic image of the fundus Ef based on the obtained detection signal. Thus, the operation of the ophthalmologic apparatus 1000 is terminated (END).

The provisional measurement in step S3 is performed as shown in FIG. 5.

(S11: Turn on Refractometry Light Source and Start Rotating Rotary Prism)

First, the main controller 211 turns on the refractometry light source 61 and starts rotating the rotary prism 66.

(S12: Analyze Ring Image)

Next, the main controller 211 controls the refractometry optical system to project a ring-shaped measurement pattern light flux onto the subject's eye E. The ring image based on the returning light of the measurement pattern light flux from the subject's eye E is imaged on the imaging surface of the imaging element 59. The main controller 211 determines whether or not the ring image based on the returning light from the fundus Ef detected by the imaging element 59 can be acquired. For example, the main controller 211 detects a position (pixel) of the edge of the image that is formed based on the returning light detected by the imaging element 59, and determines whether or not the width (difference between outer diameter and inner diameter) of the image is greater than or equal to a predetermined value. Alternatively, the main controller 211 may determine whether or not the ring image can be acquired by determining whether or not a ring can be formed based on points (image) having a predetermined height (ring diameter) or more.

When it is determined that the ring image can be acquired, the eye refractive power calculator 221 analyzes the ring image based on the returning light of the measurement pattern light flux projected onto the subject's eye E by a known method, and calculates a provisional spherical power S and a provisional astigmatic power C.

(S13: Move Focusing Lens)

Based on the provisional spherical power S and the provisional astigmatic power C which are obtained in step S12, the main controller 211 moves the refractometry light source 61, the focusing lens 74, and the liquid crystal panel 41 to positions of the equivalent spherical power (S+C/2).

(S14: Analyze Ring Image)

Again, the main controller 211 controls the refractometry optical system to project a ring-shaped measurement pattern light flux onto the subject's eye E, similar to step S12. The ring image based on the returning light of the measurement pattern light flux from the subject's eye E is imaged on the imaging surface of the imaging element 59. The main controller 211 determines whether or not the ring image based on the returning light from the fundus Ef detected by the imaging element 59 can be acquired.

When it is determined that the ring image can be acquired, the eye refractive power calculator 221 analyzes the ring image based on the returning light of the measurement pattern light flux projected onto the subject's eye E by a known method, and calculates a provisional spherical power S and a provisional astigmatic power C.

(S15: Move Focusing Lens)

Based on the provisional spherical power S and the provisional astigmatic power C which are obtained in step S14, the main controller 211 moves the refractometry light source 61, the focusing lens 74, and the liquid crystal panel 41 to positions of the equivalent spherical power (S+C/2). The position moved in step S15 is a position corresponding to the provisional far point.

(S16: Turn Off Refractometry Light Source and Stop Rotating Rotary Prism)

Next, the main controller 211 turns off the refractometry light source 61 and stops rotating the rotary prism 66. This terminates the processing of step S3 in FIG. 4 (END).

Step S4 in FIG. 4 is performed as shown in FIG. 6.

(S21: Turn on OCT Light Source and Start Operation of Optical Scanner)

First, the main controller 211 turns on the OCT light source 101 and starts operating of the optical scanner 88. With this, a predetermined site (anterior segment, fundus, or both) in the subject's eye E can be scanned with the measurement light LS. It should be noted that alignment may be performed using a known method in step S21. Further tracking may be started.

(S22: Acquire Tomographic Image)

Next, the main controller 211 sends the detection signal obtained by scanning with the measurement light LS to the image forming unit 222. The image forming unit 222 forms a tomographic image of the subject's eye E from the obtained detect signal. In case that the tomographic image is not obtained at an appropriate position, the corner cube 114 may be adjusted to adjust the position of the tomographic image.

(S23: Calculate Intraocular Parameter)

The main controller 211 controls the data processor 223 to calculate the intraocular parameter(s) from the tomographic image obtained in step S22 or the detection signal obtained by scanning in step S22. The intraocular parameter includes at least one of an axial length, a corneal thickness, an anterior chamber depth, a thickness of crystalline lens, a steeper meridian curvature radius of an anterior surface of cornea, a flatter meridian curvature radius of the anterior surface of cornea, a steeper meridian curvature radius of a posterior surface of cornea, a flatter meridian curvature radius of the posterior surface of cornea, a steeper meridian curvature radius of an anterior surface of a crystalline lens, a flatter meridian corneal thickness of the anterior surface of the crystalline lens, a steeper meridian curvature radius of a posterior surface of the crystalline lens, and a flatter meridian corneal thickness of the posterior surface of the crystalline lens.

(S24: Turn Off OCT Light Source and Stop Operation of Optical Scanner)

Next, the main controller 211 turns off the OCT light source 101 and stops the operation of the optical scanner 88. This terminates the processing of step S4 in FIG. 3 (END).

It should be noted that when it is determined that the ring image can not be acquired in step S12 or step S14, the main controller 211 moves the refractometry light source 61 and the focusing lens 74 to the minus power side (for example, −10D) or the plus power side (for example, +10D) in a preset step, considering the possibility of high refractive error of the eye. The main controller 211 controls the refractometry light reception system 7 to detect the ring image at each position. If it is still determined that the ring image can not be acquired, the main controller 211 executes a predetermined measurement error process.

In the above embodiments, the function of at least one of the relay lens 42, the focusing lenses 74 and 87 may be realized by a liquid crystal lens or a liquid lens.

Actions and Effects

Described below are the actions and effects of the ophthalmologic apparatus and the method of controlling the ophthalmologic apparatus according to the embodiments.

An ophthalmologic apparatus (1000) according to some embodiments includes a refractive power measurement optical system (refractometry optical system), a fixation projection system (4), an inspection optical system (OCT optical system 8), and a controller (210, main controller 211). The refractive power measurement optical system includes a first focusing element (focusing lens 74) capable of changing a focal position, and is configured to project first light onto a subject's eye (E) and to detect returning light of the first light from the subject's eye via the first focusing element. The fixation projection system is configured to project a fixation target onto the subject's eye. The inspection optical system includes a second focusing element (focusing lens 87) capable of changing a focal position in conjunction with the first focusing element, and is configured to perform a predetermined inspection (OCT measurement) in which second light (measurement light LS) is projected onto at least the subject's eye via the second focusing element. The controller is configured to control the first focusing element and the second focusing element based on a detection result of the returning light, and to perform refractive power measurement using the first light in a state of promoting a fogging of the subject's eye by controlling the fixation projection system after performing the predetermined inspection using the inspection optical system.

According to such a configuration, the first focusing element is controlled based on the detection result of the returning light of the first light obtained by the refractive power measurement optical system. The second focusing element is also controlled based on the above detection result, corresponding to the control of the first focusing element. Thereby, the focusing control for the refractive power measurement and the predetermined inspection is simplified. Therefore, the configuration and the control of the ophthalmologic apparatus can be simplified.

Then, after the inspection optical system performs the inspection using the second light, the refractive power measurement optical system performs the refractive power measurement using the first light. That is, the predetermined inspection is performed while the refractive power measurement. Thereby, the control for the second focusing element for performing inspection using the inspection optical system can be made unnecessary. Therefore, the time for inspection can be shorted and the burden on the subject can be reduced.

The ophthalmologic apparatus according to some embodiments further includes a holding member configured to hold the first focusing element and the second focusing element; and a driver configured to driver the holding member. The controller is configured to control the driver to move the first focusing element and the second focusing element.

According to such a configuration, the focal positions of the first focusing element and the second focusing element are moved by moving the first focusing element and the second focusing element using a single driver. Thereby, the configuration and the control of the ophthalmologic apparatus can be significantly simplified.

In the ophthalmologic apparatus according to some embodiments, the controller is configured to promote the fogging of the subject's eye by moving a focal position of an image of the fixation target in an optical axis direction of the fixation projection system from a position specified based on the detection result of the returning light (position corresponding to a provisional far point).

According to such a configuration, the fogging of the subject's eye can be promoted without controlling the first focusing element and the second focusing element.

In the ophthalmologic apparatus according to some embodiments, the fixation projection system includes a display unit (liquid crystal panel 41) configured to display the fixation target, and the controller is configured to change the focal position of the image of the fixation target by moving the display unit in the optical axis direction of the fixation projection system.

According to such a configuration, with a simple configuration, it is possible to promote the fogging of the subject's eye or to return a focal position of the subject's eye to the original position (the position specified based on the detection result of the returning light).

In the ophthalmologic apparatus according to some embodiments, the inspection optical system includes an OCT optical system (8) configured to project measurement light (LS) as the second light onto the subject's eye and to detect interference light (LC) between returning light of the measurement light from the subject's eye and reference light (LR).

According to such a configuration, the ophthalmologic apparatus capable of performing refractive power measurement and OCT measurement while reducing a burden on the subject with a simple configuration and control can be provided.

Some embodiments is a method of controlling an ophthalmologic apparatus including a refractive power measurement optical system (refractive power optical system), a fixation projection system (4), an inspection optical system (OCT optical system 8). The refractive power measurement optical system includes a first focusing element (focusing lens 74) capable of changing a focal position, and is configured to project first light onto a subject's eye (E) and to detect returning light of the first light from the subject's eye via the first focusing element. The fixation projection system is configured to project a fixation target onto the subject's eye. The inspection optical system includes a second focusing element (focusing lens 87) capable of changing a focal position in conjunction with the first focusing element, and is configured to perform a predetermined inspection in which second light (measurement light) is projected onto at least the subject's eye via the second focusing element. The method of controlling the ophthalmologic apparatus includes a focusing control step of controlling the first focusing element and the second focusing element based on a detection result of the returning light; an inspection step of controlling the inspection optical system to perform the predetermined inspection after the focusing control step; and a refractive power measurement step of performing refractive power measurement using the first light in a state of promoting a fogging of the subject's eye by controlling the fixation projection system, after the inspection step.

According to such a configuration, the first focusing element is controlled based on the detection result of the returning light of the first light obtained by the refractive power measurement optical system. The second focusing element is also controlled based on the above detection result, corresponding to the control of the first focusing element. Thereby, the focusing control for the refractive power measurement and the predetermined inspection is simplified. Therefore, the configuration and the control of the ophthalmologic apparatus can be simplified.

Then, after the inspection optical system performs the inspection using the second light, the refractive power measurement optical system performs the refractive power measurement using the first light. That is, the predetermined inspection is performed while the refractive power measurement. Thereby, the control for the second focusing element for performing inspection using the inspection optical system can be made unnecessary. Therefore, the time for inspection can be shorted and the burden on the subject can be reduced.

In the method of controlling the ophthalmologic apparatus according to some embodiments, the focusing control step is performed to move the first focusing element along an optical axis direction of refractive power measurement optical system, and to move the second focusing element along the optical axis direction of inspection optical system.

According to such a configuration, the focal positions of the first focusing element and the second focusing element are moved by moving the first focusing element and the second focusing element using a single drive control. Thereby, the configuration and the control of the ophthalmologic apparatus can be significantly simplified.

In the method of controlling the ophthalmologic apparatus according to some embodiments, in the refractive power measurement step is performed to promote the fogging of the subject's eye by moving a focal position of an image of the fixation target in an optical axis direction of the fixation projection system from a position specified based on the detection result of the returning light (position corresponding to a provisional far point).

According to such a configuration, the fogging of the subject's eye can be promoted without controlling the first focusing element and the second focusing element.

In the method of controlling the ophthalmologic apparatus according to some embodiments, the refractive power measurement step is performed to change a focal position of the image of the fixation target by moving a display unit (liquid crystal panel 41), which is configured to display the fixation target, in the optical axis direction of the fixation projection system.

According to such a configuration, with a simple configuration, it is possible to promote the fogging of the subject's eye or to return a focal position of the subject's eye to the original position (the position specified based on the detection result of the returning light).

In the method of controlling the ophthalmologic apparatus according to some embodiments, the inspection step is performed to perform OCT measurement for projecting measurement light as the second light onto the subject's eye and detecting interference light between returning light of the measurement light (LS) from the subject's eye and reference light (LR).

According to such a configuration, the method of controlling the ophthalmologic apparatus capable of performing refractive power measurement and OCT measurement while reducing a burden on the subject with a simple configuration and control can be provided.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute the method for controlling the ophthalmologic apparatus is provided. Such a program can be stored in any kind of non-transitory recording medium that can be read by the computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus, comprising:
    a refractive power measurement optical system including a first focusing element capable of changing a focal position, and configured to project first light onto a subject's eye and to detect returning light of the first light from the subject's eye via the first focusing element;
    a fixation projection system configured to project a fixation target onto the subject's eye;
    an inspection optical system including a second focusing element capable of changing a focal position in conjunction with the first focusing element, and configured to perform a predetermined inspection in which second light is projected onto at least the subject's eye via the second focusing element; and
    a controller configured to control the first focusing element and the second focusing element based on a detection result of the returning light of the first light, the returning light being obtained by performing provisional measurement using the refractive power measurement optical system in a state where the fixation target is projected onto the subject's eye, and to perform refractive power measurement using the first light in a state of promoting a fogging of the subject's eye by controlling the fixation projection system after performing the predetermined inspection using the inspection optical system.

2. The ophthalmologic apparatus of claim 1, further comprising
    a holding member configured to hold the first focusing element and the second focusing element; and
    a driver configured to driver the holding member, wherein
    the controller is configured to control the driver to move the first focusing element and the second focusing element.

3. The ophthalmologic apparatus of claim 1, wherein
    the controller is configured to promote the fogging of the subject's eye by moving a focal position of an image of the fixation target in an optical axis direction of the fixation projection system from a position specified based on the detection result of the returning light.

4. The ophthalmologic apparatus of claim 3, wherein
    the fixation projection system includes a display unit configured to display the fixation target, and
    the controller is configured to change the focal position of the image of the fixation target by moving the display unit in the optical axis direction of the fixation projection system.

5. The ophthalmologic apparatus of claim 1, wherein
    the inspection optical system includes an OCT optical system configured to project measurement light as the second light onto the subject's eye and to detect interference light between returning light of the measurement light from the subject's eye and reference light.

6. A method of controlling an ophthalmologic apparatus comprising:
    a refractive power measurement optical system including a first focusing element capable of changing a focal position, and configured to project first light onto a subject's eye and to detect returning light of the first light from the subject's eye via the first focusing element;
    a fixation projection system configured to project a fixation target onto the subject's eye; and
    an inspection optical system including a second focusing element capable of changing a focal position in conjunction with the first focusing element, and configured to perform a predetermined inspection in which second light is projected onto at least the subject's eye via the second focusing element, the method comprising:
    a focusing control step of controlling the first focusing element and the second focusing element based on a detection result of the returning light of the first light, the returning light being obtained by performing provisional measurement using the refractive power measurement optical system in a state where the fixation target is projected onto the subject's eye;
    an inspection step of controlling the inspection optical system to perform the predetermined inspection after the focusing control step; and
    a refractive power measurement step of performing refractive power measurement using the first light in a state of promoting a fogging of the subject's eye by controlling the fixation projection system, after the inspection step.

7. The method of controlling the ophthalmologic apparatus of claim 6. wherein
    the focusing control step is performed to move the first focusing element along an optical axis direction of the refractive power measurement optical system, and to move the second focusing element along the optical axis direction of the inspection optical system.

8. The method of controlling the ophthalmologic apparatus of claim 6, wherein
    the refractive power measurement step is performed to promote the fogging of the subject's eye by moving a focal position of an image of the fixation target in an optical axis direction of the fixation projection system from a position specified based on the detection result of the returning light.

9. The method of controlling the ophthalmologic apparatus of claim 8, wherein
    the refractive power measurement step is performed to change a focal position of the image of the fixation target by moving a display unit, which is configured to display the fixation target, in the optical axis direction of the fixation projection system.

10. The method of controlling the ophthalmologic apparatus of claim 6, wherein
the inspection step is performed to perform OCT measurement for projecting measurement light as the second light onto the subject's eye and detecting interference light between returning light of the measurement light from the subject's eye and reference light.

* * * * *